United States Patent
Lin et al.

(10) Patent No.: US 10,307,347 B2
(45) Date of Patent: Jun. 4, 2019

(54) BIO-CELLULOSE MEMBRANE AND METHOD FOR PRODUCING THE SAME

(71) Applicant: TCI CO., LTD, Taipei (TW)

(72) Inventors: Yung-Hsiang Lin, Taipei (TW); Cheng-Yu Ho, Taipei (TW)

(73) Assignee: TCI CO., LTD., Taipei (TW)

( * ) Notice: Subject to any disclaimer, the term of this patent is extended or adjusted under 35 U.S.C. 154(b) by 115 days.

(21) Appl. No.: 15/412,114

(22) Filed: Jan. 23, 2017

(65) Prior Publication Data
US 2017/0224592 A1     Aug. 10, 2017

(30) Foreign Application Priority Data
Feb. 5, 2016  (TW) .............................. 105103967 A

(51) Int. Cl.
| | | |
|---|---|---|
| A61K 8/02 | (2006.01) | |
| A61K 8/73 | (2006.01) | |
| A61Q 19/00 | (2006.01) | |
| C12P 19/04 | (2006.01) | |
| C12P 19/12 | (2006.01) | |
| C12P 19/18 | (2006.01) | |

(52) U.S. Cl.
CPC .......... *A61K 8/0233* (2013.01); *A61K 8/0212* (2013.01); *A61K 8/731* (2013.01); *A61Q 19/00* (2013.01); *C12P 19/04* (2013.01); *C12P 19/12* (2013.01); *C12P 19/18* (2013.01); *A61K 2800/87* (2013.01)

(58) Field of Classification Search
CPC ..... A61K 8/0233; A61K 8/731; A61K 8/0212
See application file for complete search history.

(56) References Cited

PUBLICATIONS

Kwak et al., "Bacterial Cellulose Membrane Produced by *Acetobacter* sp. A10 for Burn Wound Dressing Applications", Carbohydrate Polymers 122 (2015) 387-398. (Year: 2015).*

Wanichapichart et al., Characterization of Cellulose Membranes Produced by Acetobacter xyllinunn, J. Sci. Technol., 2002, 24(Suppl.) 855-862. (Year: 2002).*

\* cited by examiner

*Primary Examiner* — Hai Vo
(74) *Attorney, Agent, or Firm* — McClure, Qualey & Rodack, LLP

(57) ABSTRACT

A bio cellulose membrane with an outstanding water retention capacity and a method for producing the same are provided. The bio cellulose membrane comprises a first surface, a second surface, and a loose layer, wherein the average pore size of the first surface and the average pore size of the second surface are smaller than that of the loose layer.

7 Claims, 2 Drawing Sheets

BIO-CELLULOSE MEMBRANE AND METHOD FOR PRODUCING THE SAME

CLAIM FOR PRIORITY

This application claims the benefit of Taiwan Patent Application No. 105103967, filed on Feb. 5, 2016; the subject matters of which are incorporated herein by reference.

BACKGROUND OF THE INVENTION

Field of the Invention

The present invention provides a bio cellulose membrane and method for producing the same, especially a bio cellulose membrane having layers with different pore sizes and a method for producing the same.

Descriptions of the Related Art

Bio cellulose is a microfiber that is produced on the surface of a culture solution and accumulates its diameter during the culture of an acetic acid bacteria. The diameter of the bio cellulose, also known as a bacterial fiber or bacterial cellulose, is 1.3 nm. The thickness of the bio cellulose increases with culture time and then forms a bio cellulose membrane. The bio cellulose membrane protects the acetic acid bacteria from the snatch and disturbance of other bacterium and the harmful effects of ultraviolet rays.

Bio cellulose is also vinegar membrane, which is a by-product of the vinegar process and has been used in various technical fields. Since the bio cellulose membrane has an extremely smooth surface, the texture of skin, and an outstanding water retention capacity and elasticity, it is useful in cosmetic and biomedical fields, such as in the preparation of facial masks, artificial blood vessels requiring high elasticity, and artificial skin requiring high air permeability.

When using a facial mask for skin care treatment, the cosmetic liquid that moisturizes the facial mask will penetrate the skin and thus improve the appearance of the skin. However, the commercially available facial mask is made from a nonwoven fabric, and when a cosmetic liquid is applied on the nonwoven fabric, it comes into contact with a lot of air. Therefore, the efficacy of the cosmetic liquid will be significantly affected and the cosmetic liquid will be wasted due to evaporation.

SUMMARY OF THE INVENTION

Consequently, in view of such a problem, an objective of the present invention is to provide a bio cellulose membrane with an outstanding water retention capacity, which comprises a first surface, a second surface opposite to the first surface, and a loose layer between the first surface and second surface, wherein the average pore size of the first surface and the average pore size of the second surface are smaller than that of the loose layer.

In an embodiment of the present invention, the average pore size of the first surface and the average pore size of the second surface independently range from 20 to 80 nm, and the average pore size of the loose layer ranges from 50 to 150 nm.

Another objective of the present invention is to provide a method for producing a bio cellulose membrane with an outstanding water retention capacity. The method comprises the following steps: culturing a microorganism with a temperature gradient process such that the microorganism is cultured under the following temperature sequence: a first low temperature, a high temperature, and a second low temperature; and collecting the bio cellulose membrane naturally produced from the culture of the microorganism.

In an embodiment of the present invention, the microorganism is *Gluconacetobacter xylinus*.

In an embodiment of the present invention, the first low temperature and the second low temperature are the same or different, and independently range from 20 to 25° C.

In an embodiment of the present invention, the high temperature ranges from 30 to 35° C.

In an embodiment of the present invention, the culture duration at the first low temperature, the culture duration at the high temperature, and the culture duration at the second low temperature are in the ratio of 1:1:2.

The bio cellulose membrane of the present invention produced using the aforementioned temperature gradient process has a structure that is different from that of the bio cellulose membrane produced under a constant temperature. The structure significantly reduces the evaporation rate of water and thus makes the water retention capacity of the bio cellulose membrane of the present invention outstanding.

Hereinafter, embodiments of the present invention will be described with reference to accompanying drawings. However, the embodiments are for illustrative purposes only and are not intended to limit the scope of the present invention. Those skilled in the art will appreciate that various modifications, additions and substitutions are possible, without departing from the scope and spirit of the present invention as disclosed in the accompanying claims.

DESCRIPTION OF THE PREFERRED EMBODIMENT

Figure 1:
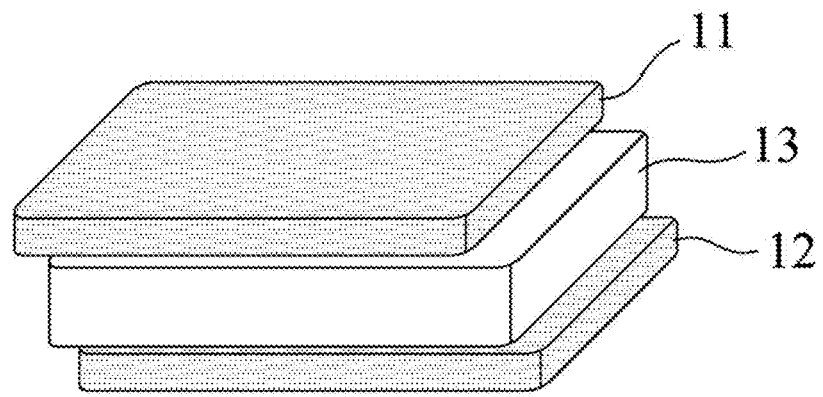
FIG. 1 is a schematic diagram showing the structure of the bio cellulose membrane of the present invention.

FIG. 1 is a schematic diagram showing the structure of the bio cellulose membrane of the present invention which has an outstanding water retention capacity. The present invention aims to provide a bio cellulose membrane with an outstanding water retention capacity, which comprises a first surface 11, a second surface 12 opposite to the first surface, and a loose layer 13 between the first surface 11 and second surface 12, wherein the average pore size of the first surface 11 and the average pore size of the second surface 12 are smaller than that of the loose layer 13.

The average pore size of the first surface 11 and the average pore size of the second surface 12 may be the same or different, but the average pore size of the first surface 11 and the average pore size of the second surface 12 are both smaller than the average pore size of the loose layer 13. The average pore size of the first surface 11 and the average pore size of the second surface 12 preferably range from 20 to 80 nm, and more preferably range from 20 to 60 nm. The average pore size of the loose layer 13 preferably ranges from 50 to 150 nm, and more preferably ranges from 50 to 120 nm.

By virtue of the property that the average pore size of the first surface 11 and the average pore size of the second surface 12 are smaller than that of the loose layer 13, when the bio cellulose membrane with an outstanding water retention capacity according to the present invention is used as a facial mask, the large pores in the loose layer 13 allow the membrane to contain a lot of cosmetic liquid, and the first surface 11 and second surface 12 with smaller average pore sizes will discourage the loose layer from losing cosmetic liquid. Therefore, the bio cellulose membrane of the present invention can significantly lower the evaporation and waste of cosmetic liquid, and increase the retention time of the cosmetic liquid on the skin.

The bio cellulose membrane with an outstanding water retention capacity according to the present invention is accomplished by using the relationship between the growth rate of an acetic acid bacteria and the culture temperature. A temperature gradient process is designed according to the relationship between the growth rate of an acetic acid bacteria and the culture temperature to obtain a bio cellulose substrate with the required dense portion (the first surface 11 and the second surface 12) and loose portion (the loose layer 13).

The acetic acid bacteria suitable for the production of the bio cellulose membrane of the present invention includes but is not limited to *Gluconacetobacter xylinus*.

Because acetic acid bacteria grows fast at high temperatures and slow at low temperatures, the inventors control the culture temperature to control the structure of the produced bio cellulose and design a culture temperature gradient to obtain a multilayer bio cellulose structure. The obtained bio cellulose membrane has a dense portion and a loose portion. The loose portion can absorb a lot of cosmetic liquid and the dense portion can improve water retention capacity and lower water evaporation rate. In an example of the present invention, *Gluconacetobacter xylinus* (BCRC12951, BCRC12952, or BCRC11682) was cultured in a culture medium (yeast extract 5.0 g, distilled water 1.0 L, peptone 3.0 g, and mannitol 25.0 g) with an inoculation amount of higher than $10^5$ under the following temperature sequence: 20 to 25° C. for 18 hours, 30 to 35° C. for 36 hours, and 20 to 25° C. for 18 hours. The inventors observed the structure of the produced bio cellulose membrane with an electron microscope and conducted a water evaporation test to determine the water retention capacity of the bio cellulose membrane of the present invention.

Figure 2A:
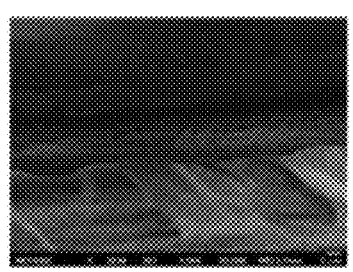
FIG. 2A is a scanning electron microscopy (SEM) photograph (10,000×) of the cross-section of the bio cellulose membrane of the present invention.
Figure 2B:
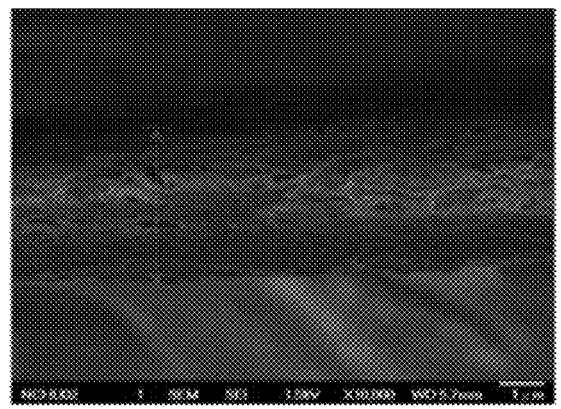
FIG. 2B is an SEM photograph (100,000×) of the cross-section of the bio cellulose membrane of the present invention.

The observing method using the electron microscope was performed according to the following process. The bio cellulose membrane sample was cleaned and subjected to a wet heat sterilization. Afterwards, the sample was cut into a proper size and dried at 60° C. The dried sample was sent to the Instrument Center of National Chung Hsing University to photograph the cross-section of the bio cellulose membrane sample by using a scanning electron microscope at 10,000× and 100,000×. The photographs are shown in FIG. 2A and FIG. 2B. FIG. 2A is the SEM photograph at 10,000× of the cross-section of the bio cellulose membrane of the present invention, while FIG. 2B is the SEM photograph at 100,000× of the cross-section of the bio cellulose membrane of the present invention. The double arrow symbol in FIG. 2B is used to denote the bio cellulose membrane of the present invention.

Figure 2C:
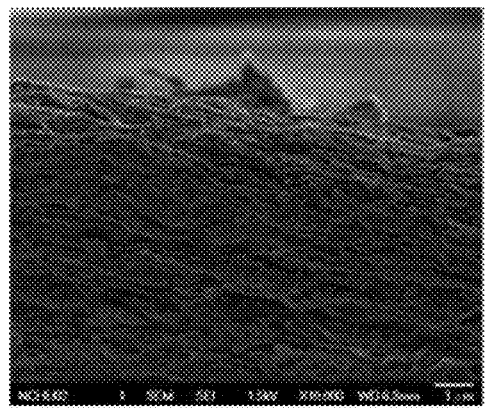
FIG. 2C is an SEM photograph of the cross-section of a comparative bio cellulose membrane.

As can be seen from the figures, the SEM observation manifests that the bio cellulose membrane cultured using the temperature gradient process has a layered structure with layers having different fiber densities. The bio cellulose membrane has a first surface 11, a second surface 12 opposite to the first surface, and a loose layer 13 between the first surface 11 and second surface 12, wherein the average pore size of the first surface 11 and the average pore size of the second surface 12 are smaller than that of the loose layer 13. A comparative bio cellulose membrane was produced as a control group by culturing the acetic acid bacteria at a constant temperature (30° C.). The SEM photograph of the cross-section of the comparative bio cellulose membrane is shown in FIG. 2C. As can be seen from the comparison of FIGS. 2A, 2B, and 2C, the culture at a constant temperature results in a homogeneous bio cellulose membrane structure while the culture using the temperature gradient process results in a layered structure with layers having different fiber densities.

Figure 3:
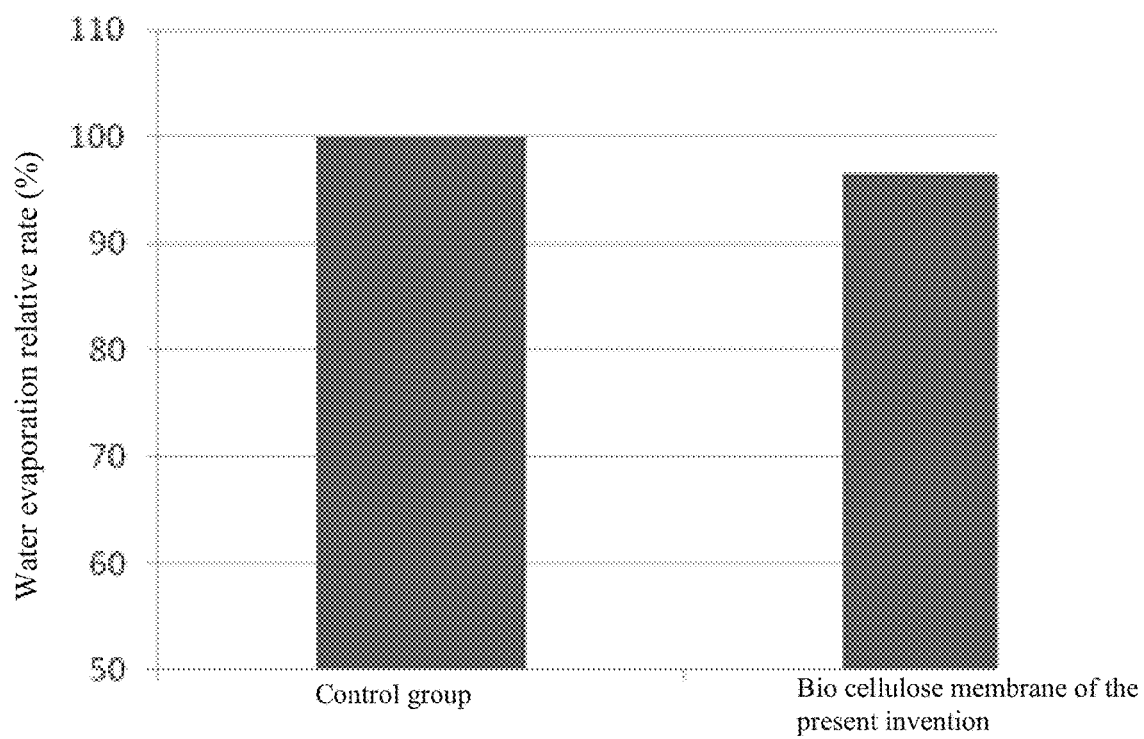
FIG. 3 is a chart showing the water evaporation test result of the bio cellulose membrane of the present invention.

The water evaporation test was performed according to the following process. Bio cellulose substrates with identical sizes were allowed to stand at room temperature. The substrates were weighed per 10 minutes to calculate water evaporation rate. A bio cellulose membrane produced by culturing the acetic acid bacteria at 30° C. was used as a control group. The results of the water evaporation test are shown in FIG. 3. The water evaporation rate of the bio cellulose membrane of the present invention is 11 mg/min while the water evaporation rate of the control group is 11.39 mg/min. The results manifest that under the same water evaporation area, the bio cellulose membrane of the present invention produced using the temperature gradient process has a lower water evaporation rate. Since the area of a human face is very small, a little improvement on the retention time of water is sufficient to significantly improve the efficacy of a facial mask.

As can be seen from the aforementioned example, the observation using a scanning electron microscope manifests that the structure of the bio cellulose membrane cultured using a temperature gradient process is obviously different from that of the bio cellulose membrane cultured at a constant temperature. The water evaporation rate of the bio cellulose membrane cultured using a temperature gradient process is slower than that of the bio cellulose membrane cultured at a constant temperature. Therefore, the bio cellulose membrane of the present invention has a high water retention structure and thus an outstanding water retention capacity.

The bio cellulose membrane of the present invention can be used as the substrate of a functional bio cellulose facial mask, and can significantly lower the water evaporation of cosmetic liquid and keep the substrate wet for a long time. At present, the production of a bio cellulose membrane never focuses on the precise control of the culture temperature. Although the cosmetic liquid absorption performance of the bio cellulose membrane cultured at a constant temperature is already good, the bio cellulose membrane of the present invention not only provides a good cosmetic liquid absorption performance but also effectively lowers the evaporation of water and therefore has an outstanding moisture/water retention capacity.

The bio cellulose membrane of the present invention is useful in various industries. For example, the bio cellulose membrane of the present invention can be used in food (e.g., coconut jelly), medical material (e.g., wound dressing and artificial skin), and the paper industry (e.g., paper and membranes for earphones).

What is claimed is:

1. A bio cellulose membrane having a water retention capacity, comprising
a first surface, a second surface opposite to the first surface, and a loose layer between the first surface and second surface,
wherein the first surface, the second surface and the loose layer are made of the same material produced from a microbial culture of acetic acid microorganism, the average pore size of the first surface and the average pore size of the second surface independently range from 20 to 80 nm, the average pore size of the loose layer ranges from 50 to 150 nm, and the average pore size of the first surface and the average pore size of the second surface are smaller than that of the loose layer.

2. A method for producing the bio cellulose membrane of claim 1, comprising:
culturing the acetic acid microorganism with a temperature gradient process such that the microorganism is cultured under the following temperature sequence: a first low temperature, a high temperature, and a second low temperature;
collecting the bio cellulose membrane naturally produced from the culture of the microorganism;
wherein the first low temperature and the second low temperature independently range from 20° C. to 25° C.; and
wherein the high temperature ranges from 30° C. to 35° C.

3. The method of claim 2, wherein the microorganism is *Gluconacetobacter xylinus*.

4. The method of claim 2, wherein the first low temperature and the second low temperature are the same or different.

5. The method of claim 2, wherein the culture duration at the first low temperature, the culture duration at the high temperature, and the culture duration at the second low temperature are in the ratio of 1:1:2.

6. The method of claim 5, wherein the culture duration at the first low temperature and the culture duration at the second low temperature are 18 hours respectively.

7. The method of claim 5, wherein the culture duration at the high temperature is 36 hours.

* * * * *